United States Patent [19]
Scheler et al.

[11] Patent Number: 5,834,157
[45] Date of Patent: Nov. 10, 1998

[54] 2-ACYLAMINO-9-ARYLACRIDINES, PROCESS FOR THEIR PREPARATION AND PHOTOSENSITIVE MIXTURES CONTAINING THEM

[75] Inventors: Siegfried Scheler, deceased, late of Wiesbaden, by Rosemarie Scheler, Heir; Klaus-Peter Bergmann, Mainz; Gerhard Buhr, Koenigstein, all of Germany

[73] Assignee: Agfa-Gevaert AG, Leverkusen, Germany

[21] Appl. No.: 772,254

[22] Filed: Dec. 23, 1996

[30] Foreign Application Priority Data

Dec. 23, 1995 [DE] Germany ............ 195 48 623.4

[51] Int. Cl.⁶ .................................. G03F 7/031
[52] U.S. Cl. ............... 430/281.1; 430/915; 430/916; 430/920; 430/288.1; 522/63; 522/106; 522/107; 522/121; 546/104
[58] Field of Search ............... 546/104; 522/63, 522/106, 107, 121; 430/281.1, 288.1, 915, 916, 920

[56] References Cited

U.S. PATENT DOCUMENTS

| | | | |
|---|---|---|---|
| 3,272,635 | 9/1966 | Sprague et al. | 426/234 |
| 3,751,259 | 8/1973 | Bauer | 430/288.1 |
| 4,019,972 | 4/1977 | Faust | 430/283.1 |
| 5,217,845 | 6/1993 | Steppan et al. | 430/281 |

FOREIGN PATENT DOCUMENTS

| | | |
|---|---|---|
| 1 283 091 | 11/1968 | Germany . |
| 2 328 195 | 1/1974 | Germany . |
| 1 354 541 | 5/1974 | United Kingdom . |

OTHER PUBLICATIONS

Ullmann E. Chem. Ber. 39, 303, 1906.

Bedair, et al., "Synthesis of some derivatives of 4–acetylamino–3–nitrobenzenesulfonic acid, part 2", Acta Pharm. Jugosl, 37 (1987), pp. 157–163.

Carde, et al., "Intramolecular Nitrene Insertions into Aromatic and Heteroaromatic Systems. Part 4. Insertions using Triphenylmethanes, Unactivated or Bearing Electron–donating Groups", Journal of the Chemical Society, 1978, pp. 1211–1218.

*Primary Examiner*—Evelyn Huang
*Attorney, Agent, or Firm*—Foley & Lardner

[57] ABSTRACT

Compounds of the formula

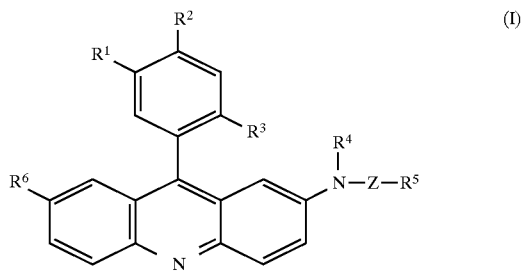

are suitable as photoinitiators in free-radical-polymerizable mixtures and are notable for a reduced tendency to diffusion and sublimation than comparable known compounds.

18 Claims, No Drawings

2-ACYLAMINO-9-ARYLACRIDINES, PROCESS FOR THEIR PREPARATION AND PHOTOSENSITIVE MIXTURES CONTAINING THEM

BACKGROUND OF THE INVENTION

1. Field of the Invention

The present invention relates to 2-acylamino-9-arylacridines, processes for their preparation, and photosensitive mixtures which include these compounds.

2. Description of Related Art

DE-C 20 27 467 discloses photopolymerizable mixtures which contain polymeric binders, free-radical-polymerizable compounds containing at least one terminal ethylenically unsaturated group and having a boiling point above 100° C. at normal pressure, and a 9-arylacridine compound as a photoinitiator. Of the 9-arylacridine compounds, 9-phenylacridine is particularly notable for its high photosensitivity. This compound and other preferred representatives of this class have the disadvantage that they tend to migrate or diffuse out of photopolymerizable mixtures which are in contact with polyethylene sheets. The initiators diffuse into the polyethylene sheets and through them. As a result, the layer becomes depleted in initiator and loses sensitivity.

A further disadvantage of the known mixtures is that they lose photoinitiator by sublimation. This is particularly noted in the case of applications for which photosensitive mixtures are heated at fairly high temperature for a fairly long time in the course of the processing, for example, in the preparation of solder resist masks (solder masks). The loss of photoinitiaor by sublimation may result, on the one hand, in loss of photosensitivity if a photocrosslinking step is still to follow. It also results, however, in contamination and/or corrosion of the processing equipment and of the electronic components to be produced therewith.

EP-A 374 704 describes 9-arylacridines which are substituted in position 2 by an alkyl group or an acyl group and which are suitable as photoinitiators in photopolymerizable mixtures. Such mixtures have a reduced tendency to diffusion and a reduced tendency to bleed in acidic electroplating baths than unsubstituted 9-arylacridines. A lower tendency to sublimation is not described for these compounds.

SUMMARY OF THE INVENTION

An object of the present invention was to provide substituted 9-arylacridines which are suitable as photoinitiators in photopolymerizable mixtures.

It was also an object of the invention to provide methods of making such compounds and methods of using such compounds.

In accordance with these and other objectives, there are provided novel compounds of the formula I

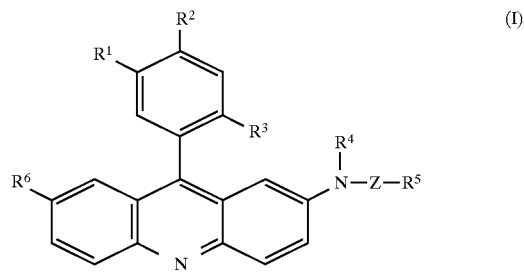

wherein $R^1$, $R^2$, $R^3$ and $R^6$ are identical to or different from one another and are selected from the group consisting of hydrogen, halogen atoms, $C_1$–$C_6$ alkyl, $C_1$–$C_6$ alkoxy, and $C_1$–$C_6$ alkoxyalkyl groups;

$R^4$ is a hydrogen atom, an alkyl group containing 1 to 4 carbon atoms or an $SO_2R^5$ radical;

$R^5$ is an alkyl, alkoxy, alkoxyalkyl, carboxyalkyl or alkenyl group containing up to 6 carbon atoms, an aralkyl group containing 7 to 10 carbon atoms or an aralkenyl group containing 8 to 10 carbon atoms; and Z is a carbonyl or sulfonyl group.

In further accordance with these and other objectives, there is provided a photopolymerizable mixture including a compound of the above formula I as a photoinitiator.

In yet further accordance with these and other objectives, there is provided a process for preparing a compound of formula I which comprises converting 2-chloro-5-nitrobenzoic acid into an acid chloride using a chlorinating agent;

reacting the acid chloride with a compound of formula II

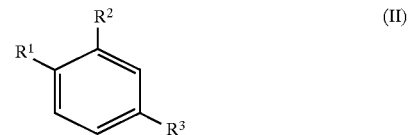

in the presence of a Friedel-Crafts catalyst to form a substituted benzophenone of formula III;

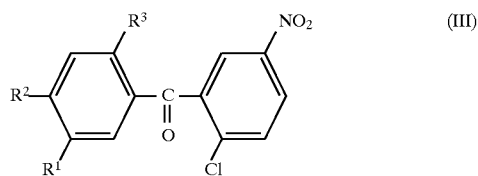

replacing the 2-chlorine atom of the compound III by an anilino radical by reacting the benzophenone of formula III with an aromatic amine of formula IV,

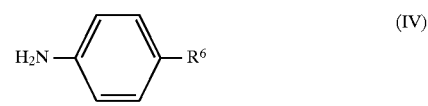

to form a secondary amine of formula V;

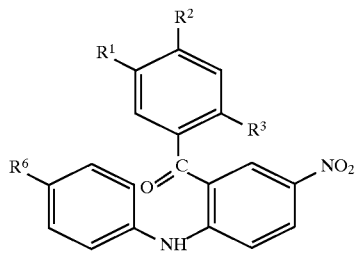

cyclizing the secondary aromatic amine of formula V, to form 2-nitro-9-arylacridine of formula VI;

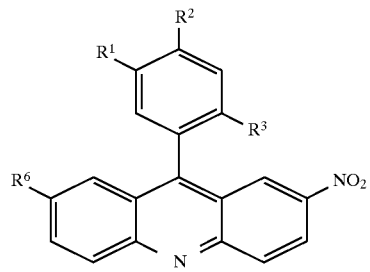

reducing the 2-nitro-9acylacridine compound VI to the corresponding primary amine (VII)

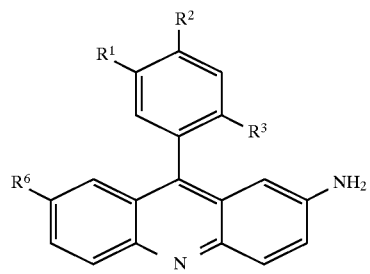

reacting the amine VII with an acylating agent $R^5$—Z—X, and optionally with a further acylating agent or an alkylating agent $R^4$—X, where X is a halogen atom, to form the compound of the formula I.

Further objects, features and advantages of the invention will become apparent from the detailed description that follows.

DETAILED DESCRIPTION

The compounds of the invention can be used in any desired photopolymerizable mixture. A photopolymerizable mixture according to the present invention preferably comprises a polymeric binder, an ethylenically unsaturated, free-radical polymerizable compound and a compound of the above formula I as a photoinitiator. Any desired binders and polymerizable compounds can be used. When compounds of the present invention are used in photopolymerizable mixtures, in particular for the preparation of photoresists and solder masks, not only do the compounds have a reduced tendency to diffusion, but they also have a reduced tendency to sublime from the layer at elevated temperature in both the unexposed and exposed state.

If $R^1$, $R^2$, $R^3$ and/or $R^6$ are halogen atoms in the compounds according to the invention, they are preferably chlorine atoms or bromine atoms, in particular chlorine atoms. As alkyl groups, those having 1 to 4, in particular 1 or 2 carbon atoms, especially methyl groups, are particularly preferred. As alkoxy or alkoxyalkyl groups, those having up to 4, particularly up to 2 carbon atoms are also particularly advantageous. Of these radicals, at least one is preferably a hydrogen atom.

$R^4$ is preferably hydrogen, but may also be a low alkyl group containing 1 to 4 carbon atoms, preferably 1 or 2 carbon atoms, in particular a methyl group. Alternatively, $R^4$ may comprise an $R^5SO_2$ group, preferably an alkanesulfonyl, in particular methanesulfonyl group.

$R^5$ may be an alkyl group containing 1 to 6, preferably 1 to 4, in particular 1 or 2 carbon atoms or an alkoxy or alkoxyalkyl group of similar chain length. $R^5$ carboxyalkyl or alkenyl groups may contain 2 to 6, preferably 2 to 4 carbon atoms. Benzyl groups are preferred as aralkyl groups, and phenylethenyl groups are preferred as aralkenyl groups. Z may be either a carbonyl or sulfonyl group, and is most preferably a carbonyl group.

The compounds according to the invention are prepared in a sequence of steps which are easy to carry out with high yield. In a useful process, first the 2-chloro-5-nitrobenzoic acid is converted into a carboxylic chloride using a chlorinating agent such as, for example, phosphorus pentachloride or, preferably, using thionyl chloride in the presence of N-methylmorpholine. Usually, without intermediate isolation, the latter is reacted with the aromatic compound II with a Friedel-Crafts catalyst such as anhydrous $FeCl_3$ being added to form the correspondingly substituted benzophenone (III). The reaction product generally precipitates in very pure crystalline form from the reaction mixture, which is preferably diluted with a polar solvent, for example, ethanol.

The compound III is reacted with an aromatic amine IV, preferably at an elevated temperature (generally 130°–170° C., preferably 150°–160° C.), in the presence of sodium acetate to form a diphenylamine derivative of formula (V). This product also generally precipitates in high purity and with good yield from the diluted reaction mixture. It is also possible to employ other weak bases, e.g., sodium carbonate, which are customary for nucleophilic aromatic substitution reactions employing amines as nucleophilic compounds, instead of the sodium acetate. These other bases are usually employed in about equimolar amounts.

The compound V is cyclized, preferably in an acidic reaction medium, for example, a glacial acetic acid/concentrated sulfuric acid mixture, at an elevated temperature (generally 100°–140° C., preferably 110°–125° C.), to form an acridine derivative of formula (VI) (2-nitro-9-phenylacridine).

The 2-nitro-9-phenylacridine is then reduced to the primary amine (VII). The reduction may be carried out in an ethanol/concentrated hydrochloric acid mixture with $SnCl_2$ or in strongly acidic aqueous solution (pH≦1) with metallic aluminum such as aluminum shot. The latter method has the advantage that substantially no environmentally contaminating heavy-metal salts are produced. The compound VII is also obtained in high yield.

Finally, the primary amine VII is acylated with an acylating agent such as carboxylic anhydride (such as acetic, succinic or methacrylic anhydride), a carboxylic acid halide, in particular, a carboxylic acid chloride (for example, methoxyacetyl, phenylacetyl, cinnamyl or benzoyl chloride), a carboxylic ester chloride (for example, ethyl chloroformate) or an alkyl- or arylsulfonyl chloride. The acylation may optionally be conducted in a solvent and optionally in the presence of a tertiary base, such as triethylamine, pyridine, N-methylmorpholine or 1,4-diazabicyclo[2.2.2]octane, to form the compound I. Compounds in which $R^4=R^5Z$ are most easily obtained under suitable conditions using an excess of acylating agent. $R^4$ alkyl radicals can also be introduced before the acylation using an alkylating agent. $R^4 \neq R^5Z$ acyl radicals can be produced in a separate acylating step before or after the $R^5Z$ radical.

The compounds according to the invention have an outstanding activity as free-radical-forming photoinitiators. Their activity is essentially equal to that of the unsubstituted 9-phenylacridine which is described in DE-C 20 27 467.

To prepare photopolymerizable mixtures according to the present invention, the initiators are preferably dissolved together with an organic polymeric binder, a free-radical-polymerizable ethylenically unsaturated compound, and optionally, with further standard constituents in a suitable solvent. The solution obtained is applied to a layer base and dried to form a photopolymerizable layer. The quantitative proportion of the compounds of the formula I in the mixture according to the invention is preferably 0.01 to 10, more preferably 0.1 to 5% by weight, relative to the total weight of the nonvolatile constituents.

Suitable polymerizable compounds for the purposes of the invention are known and are described, for example, in U.S. Pat. No. 2,760,863 and No. 3,060,023. Preferred examples include acrylic and methacrylic esters of monohydric or polyhydric, preferably at least dihydric alcohols, such as ethylene glycol diacrylate, polyethylene glycol dimethacrylate, acrylates and methacrylates of trimethylolethane, trimethylolpropane, pentaerythritol and dipentaerythritol and of polyhydric alicyclic alcohols, or N-substituted acrylic and methacrylic amides. Advantageously, reaction products of mono- or diisocyanates with partial esters of polyhydric alcohols may also used. Such monomers are described in DE-A 20 64 079, 23 61 041 and 28 22 190. The quantitative proportion of monomers in the mixture is generally about 10 to 80, preferably 20 to 60% by weight, relative to the total weight of the non-volatile constituents.

The mixture generally also contains, in addition, a polymeric binder. A multiplicity of organic polymers which are soluble in a coating solvent can be used as binders. As examples, mention may be made of: polyamides, polyvinyl esters, polyvinyl acetals, polyvinyl ethers, epoxy resins, polyacrylic esters, polymethacrylic esters, polyesters, alkyd resins, polyacrylamide, polyvinyl alcohol, polyethylene oxide, polydimethylacrylamide, polyvinylpyrrolidone, polyvinylmethylformamide, polyvinylmethylacetamide and also copolymers of the monomers which form the homopolymers enumerated.

Further, natural substances or modified natural substances, for example gelatines and cellulose ethers, are suitable as binders.

Particularly advantageously, binders are used which are insoluble in water, but soluble, or at least swellable in aqueous alkaline solutions, since layers containing such binders can be developed with the preferred aqueous alkaline developers. Such binders may contain, for example, one or more of the following groups: —COOH, —PO$_3$H$_2$, —SO$_3$H; —SO$_2$NH—, —SO$_2$—NH—SO$_2$— and —SO$_2$—NH—CO—.

As examples of these, mention may be made of maleate resins, polymers of β-(methacryloyloxy) ethyl N-(p-tolylsulfonyl)carbamate and copolymers of the latter and similar monomers with other monomers, and also vinylacetate/crotonic acid and styrene/maleic anhydride copolymers. Alkyl methacrylate/methacrylic acid copolymers and copolymers of methacrylic acid, higher alkyl methacrylates and methyl methacrylate and/or styrene, acrylonitrile, inter alia, as described in DE-A 20 64 080 and 23 63 806, are particularly preferred. The "higher alkyl methacrylates" contain at least 4, preferably 4 to 15, carbon atoms in their alkyl part.

The amount of binder is preferably in the range from 20% to 90%, more preferably 40% to 80% by weight, based on the total weight of the mixture.

Depending on the planned application and depending on the desired properties, the photopolymerizable mixtures may contain various substances as additives. Examples include: inhibitors for preventing the thermal polymerization of the monomers, hydrogen donors, substances which modify the spectral photosensitivity of such substances, dyes, colored and colorless pigments, color forming agents, indicators, plasticizers, for example polyglycols or esters of p-hydroxybenzoic acid.

These constituents can be expediently selected so that they absorb as little as possible in the actinic radiation range important for the initiation process.

Within the scope of this description, any radiation whose energy is equal at least to that of shortwave visible light, is to be understood as "actinic radiation". Longwave UV radiation and also electron, X-ray and laser radiation are suitable as radiation sources.

The photopolymerizable mixture of the present invention can be used for the many varied applications. For example, the mixtures are useful for producing safety glass, lacquers which are cured by light or corpuscular beams, such as electron beams, in the dental field and, in particular, as photosensitive recording materials in the reproduction field.

Although the present detailed description of the invention is focused on photosensitive recording materials for the reproduction field, the invention is not limited thereto. As possible applications in this field, mention may be made of: recording layers for the photomechanical production of printing forms for letter-press printing, planographic printing, gravure printing, screen printing, relief copies, for example production of texts in braille, individual copies, tan formers, pigment formers, etc. Furthermore, the mixtures can be used for the photomechanical production of etching resists, for example, for the manufacture of nameplates, and of printed circuits, and for chemical milling. The mixtures according to the invention have particular significance as copying layers for the photomechanical production of planographic printing forms and for photoresist technology.

The mixtures of the present invention can be used industrially for the application fields mentioned in the form of a liquid solution of dispersion, for example, as a photoresist solution, which is applied by the user himself to an individual base, such as for chemical milling. In addition, mixtures of the present invention can also be used for producing printed circuits, for screen-printing templates and the like. As a solid photosensitive layer on a suitable base, the mixture can also be in the form of a storable precoated photosensitive copying material, for example, for producing printing forms. Mixtures of the present invention are also suitable for producing dry resist.

It is generally beneficial to substantially remove the mixtures from the influence of atmospheric oxygen during the photopolymerization. If the mixture is used in the form of thin copying layers, it is advisable to apply a suitable top film of low permeability for oxygen. The latter can be self-supporting and peeled off before the development of the copying layer. Polyester films, for example, are suitable for this purpose. The top film may also be composed of a material which dissolves in the developer liquid or which can at least be removed at the uncured areas during the development. Suitable materials for this purpose include, for example, waxes, polyvinyl alcohol, polyphosphates, sugar, and the like.

Suitable as layer bases for copying materials produced with the mixture according to the invention include, for example, aluminum, steel, zinc, copper and plastic sheets, for example of polyethylene terephthalate or cellulose acetate, and also screen-printing bases, such as Perlon gauze.

The photosensitive materials are produced in a known manner using the mixture according to the invention.

Thus, a mixture according to the present invention can preferably be taken up in a solvent and the solvent or dispersion applied to the base provided as a film by casting, spraying, immersion, application with rolls etc. and then dried. Thick layers (for example, of 250 µm and over) are advantageously produced by extrusion or press molding as a self-supporting sheet, which is then optionally laminated onto the base. In the case of dry resist, solutions of the mixture are applied to transparent bases and dried. The photosensitive layers (thickness approximately between 10 and 100 µm) are then likewise first laminated onto the desired substrate by lamination together with the temporary base.

The materials can be processed in a known manner. For the development, they are treated with a suitable developer solution, preferably a weakly alkaline, aqueous solution, wherein the unexposed portions of the layer are removed and the exposed areas of the copying layer remain behind on the base.

The recording materials according to the invention are notable for a lower photosensitivity loss during storage. This advantage is apparently brought about by a higher diffusion resistance of the initiators in the photopolymerizable layer than in the case of the unsubstituted 9-phenylacridine. Recording materials of the present invention have the further advantage that the photoinitiators contained in them do not substantially sublime (or at least sublime to a substantially lesser extent than the hitherto known initiators of comparable efficiency) from the unexposed or exposed layer even at fairly high temperatures up to, and above about 200° C.

Examples of the mixture according to the invention are specified below. In this specification, the preparation of compounds of the formula I is first described. Then examples are given of the application of the novel compounds in photopolymerizable mixtures.

In the examples, parts by weight (pbw) and parts by volume (pbv) are in the relationship of g to ccm. Unless otherwise specified, percentage and quantitative ratios are in units of weight.

The examples are for illustrative purposes only and do not limit the scope of the invention.

Preparation Example 1

Preparation of 2-acetylamino-9-(2,5-dimethylphenyl) acridine (compound 1)

a) 2-Chloro-5-nitro-2',5'-dimethylbenzophenone (compound 1a). 203.5 pbw of 2-chloro-5-nitrobenzoic acid were introduced while stirring into 144.2 pbw of thionyl chloride and 0.5 pbv of N-methylmorpholine were added. The suspension was heated to boiling and stirred for 3½ hours under reflux. During the reaction, the boiling point rose from 66°–67° C. to approximately 100°–102° C. and a clear greenish yellow solution was formed. After completion of the reaction, the mixture was cooled to 70°–75° C. and the excess thionyl chloride removed in vacuo. Then 116.6 pbw of p-xylene and 3 pbw of anhydrous $FeCl_3$ were added, the yellowish brown solution was heated to 100°–102° C. and stirred for 3 hours at this temperature with hydrogen chloride being evolved. After switching off the heating, 500 pbv of ethanol were added to the still hot reaction mixture and the mixture was allowed to cool to 25° C. in the course of 4 hours. The precipitated product was filtered off by suction, washed with ethanol and then with water and dried for 24 hours at 40° C. in a circulating-air oven. Yield: 262 pbw (90.5% of theory) of light yellow needles. Mp.: 89°–91° C.

b) 2-Anilino-5-nitro-2',5'-dimethylbenzophenone (compound 1b) 144.7 pbw of 2-chloro-5-nitro-2',5'-dimethylbenzophenone and 41.8 pbw of anhydrous sodium acetate were suspended in 140.2 pbw of aniline (99.5% strength) and heated at 150°–160° for 2½ hours while stirring. The water formed during the reaction was distilled off in this process. The yellowish brown, turbid solution was cooled to 70° C. and 500 pbv of ethanol were added. After standing overnight, the yellow precipitate was filtered off by suction, washed with ethanol and then with water and dried at 50° C. in a circulating-air oven. Yield: 164 pbw (95% of theory), yellow crystals. Mp.: 127°–129° C.

c) 2-Nitro-9-(2,5-dimethylphenyl)acridine (compound 1c) 173 pbw of 2-anilino-5-nitro-2',5'-dimethylbenzophenone were suspended in 1,250 pbw of glacial acetic acid. 66 pbv of sulfuric acid (96% strength) were added to the suspension and the whole was heated at 118°–119° C. for 6 hours while stirring well. The yellow solution was added dropwise to 10,000 pbv of water, and the yellow precipitate formed was filtered off by suction, washed well with water and dried for 24 hours at 100° C. in vacuo. Yield: 161 pbw (98% of theory), yellow powder. Mp.: 171°–173° C.

d) 2-Amino-9-(2,5-dimethylphenyl)acridine (compound 1d) 20 pbw of $SnCl_2 \times 2\ H_2O$ were dissolved in 50 pbv of ethanol at 60° C. and 4.1 pbw of 2-nitro-9-(2,5-dimethylphenyl)acridine were stirred into the solution. The temperature rose to 75°–76° C. during this process. 17 pbv of hydrochloric acid (38% strength) were added dropwise to the deep-red solution and stirring of the whole was continued for 30 minutes at 72°–75° C. Then a further 4.1 pbw of the acridine derivative were added and stirring of the mixture was continued for 10 minutes at 72°–75° C. after adding 26 pbv of 38% strength hydrochloric acid dropwise. The mixture was then heated to boiling for 30 minutes, stirred into 850 pbv of water and 85 pbv of 25% strength ammonia solution and extracted by shaking with methylene chloride. After the organic phase had been dried over anhydrous sodium sulfate, the solvent was distilled off. The red residue was ground with diethyl ether, filtered off by suction and dried in vacuo. Yield: 6.7 pbw (90% of theory), orange powder. Mp.: 162°–164° C.

e) 2-Acetylamino-9-(2,5-dimethylphenyl)acridine (compound 1) 70 pbw of 2-amino-9-(2,5-dimethylphenyl) acridine were dissolved in 70 pbv of acetic anhydride and 0.5 pbv of N-methylmorpholine (99% strength) was added. The orange solution was stirred for 30 minutes at 27° C., after that for a further 30 minutes at 50° C. and then poured into 250 pbv of water. After adding 150 pbv of 25% strength ammonia solution, the precipitate was filtered off by suction and dried for 24 hours at 40° C. in a circulating-air oven. Yield: 6.9 pbw (85.5% of theory), yellow crystals. Mp.: 236°–238° C.

Preparation Example 2

Preparation of 2-benzoylamino-9-(2,5-dimethylphenyl)acridine (compound 2).

2.98 pbw of 2-amino-9-(2,5-dimethylphenyl)acridine (compound 1d) were dissolved in 75 pbv of methylene chloride at 23° C. and 2.1 pbw of benzoyl chloride were gradually added while stirring. The temperature rose to 27°–28° C. during this process. The solution was stirred for 4 hours and, after standing overnight, extracted by shaking with sodium hydroxide solution, and the organic phase was distilled off after drying over anhydrous sodium sulfate. Yield: 3.96 pbw (98% of theory), yellowish green crystals. Mp.: 253°–255° C.

Preparation Example 3

Preparation of 2-ethyloxycarbonylamino-9-(2,5-dimethylphenyl)acridine (compound 3).

1.42 pbw of the compound 1d and 2.78 pbw of ethyl chloroformate were dissolved in 100 pbv of acetonitrile at 25° C. and 4.85 pbv of N-methylmorpholine were added. The temperature rose to 38° C. during this process. Stirring of the yellow solution was continued for 15 minutes, then it was poured into 400 pbv of water, and the mixture was stirred for 2 hours and the precipitated residue filtered off by suction. Yield: 1.3 pbw (72% of theory). Mp.: 200°–202° C.

Preparation Example 4

Preparation of 2-[N,N-bis(methanesulfonyl)amino]-9-(4-methylphenyl)acridine (compound 12).

5.68 pbw of 2-amino-9-(4-methylphenyl)acridine (compound 12d) were dissolved with 20.3 pbw of methanesulfonyl chloride and 22.4 pbw of diazabicyclo[2.2.2]octane in 120 pbv of acetonitrile and the solution heated for 2 hours under reflux. After cooling to 20° C., filtration was carried out and the red filtrate added dropwise to 1000 pbv of 0.5% strength ammonia solution. After standing overnight, the precipitate was filtered off by suction and crystallized from 135 pbv of ethanol. Yield: 1.76 pbw (20% of theory), light yellow needles. Mp.: 217°–219° C.

Preparation Examples 5 to 20

Compounds of the formula

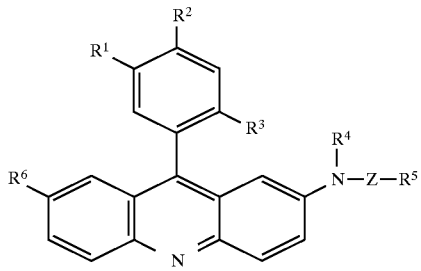

(I)

where $R^4$=H in all cases, were prepared analogously to Example 1. The melting points of the compounds 4 to 11 and 13 to 20 and of their intermediates are listed in Tables I to V below. The yield data relate to the stage concerned. The numeral designating the intermediates corresponds to the final product or products prepared from them; the letter indicates the process stage concerned (a to d).

Table I—Intermediates of stage (a)
Table II—Intermediates of stage (b)
Table III—Intermediates of stage (c)
Table IV—Intermediates of stage (d)
Table V—Final products—stage (e)

TABLE I

Compounds of the formula

| Compound No. | $R^1$ | $R^2$ | $R^3$ | Mp., °C. | Yield % | Appearance |
|---|---|---|---|---|---|---|
| 4a | H | H | H | 76–79 | 15 | colorless crystals |
| 5a, 10a–13a | H | $CH_3$ | H | 95–97 | 68.5 | light yellow crystals |
| 6a | H | $CH_3$ | $CH_3$ | 97–99 | 78.5 | light yellow needles |
| 7a | H | Cl | H | 94–96 | 84 | colorless crystals |
| 8a | H | $OCH_3$ | H | 107–110 | 47 | colorless crystals |
| 9a | H | $t-C_4H_9$ | H | 151–153 | 66 | colorless crystals |

TABLE II

Compounds of the formula

| Compound No. | $R^1$ | $R^2$ | $R^3$ | $R^6$ | M.p., °C. | Yield, % | Appearance |
|---|---|---|---|---|---|---|---|
| 4a | H | H | H | H | 130–136 | 50.5 | yellow needles |
| 5b, 10b–13b | H | $CH_3$ | H | H | 124–128 | 96 | yellow crystals |
| 6b | H | $CH_3$ | $CH_3$ | H | 130–132 | 87.5 | yellow crystals |
| 7b | H | Cl | H | H | 123–126 | 57.5 | yellow powder |
| 8b | H | $OCH_3$ | H | H | 149–151 | 85 | yellow crystals |
| 9b | H | $t-C_4H_9$ | H | H | — | 96 | yellow oil |
| 18b | $CH_3$ | H | $CH_3$ | $CH_3$ | 130–132 | 91 | yellow powder |
| 19b | $CH_3$ | H | $CH_3$ | $OCH_3$ | 144–146 | 92 | orange powder |
| 20b | $CH_3$ | H | $CH_3$ | Cl | 177–179 | 65 | yellow powder |

TABLE III

Compounds of the formula

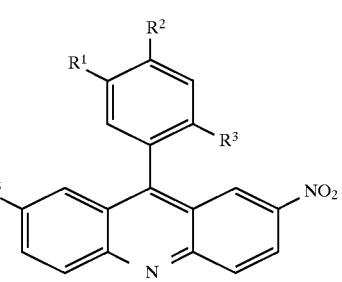

| Compound No. | $R^1$ | $R^2$ | $R^3$ | $R^6$ | M.p. (°C.) | Yield (%) | Appearance |
|---|---|---|---|---|---|---|---|
| 4c | H | H | H | H | 212–214 | 44 | yellow crystals |
| 5c, 10c–13c | H | $CH_3$ | H | H | 202–204 | 95.5 | yellow powder |
| 6c | H | $CH_3$ | $CH_3$ | H | 146–147 | 92.5 | yellow powder |
| 7c | H | Cl | H | H | 220–222 | 94 | yellow powder |
| 8c | H | $OCH_3$ | H | H | 178–180 | 85 | yellow powder |
| 9c | H | t-$C_4H_9$ | H | H | 242–244 | 80 | yellow powder |
| 18c | $CH_3$ | H | $CH_3$ | $CH_3$ | 195–197 | 98 | yellow powder |
| 19c | $CH_3$ | H | $CH_3$ | $OCH_3$ | 185–187 | 98 | yellow powder |
| 20c | $CH_3$ | H | $CH_3$ | Cl | 210–212 | 98 | yellow powder |

TABLE IV

Compounds of the formula

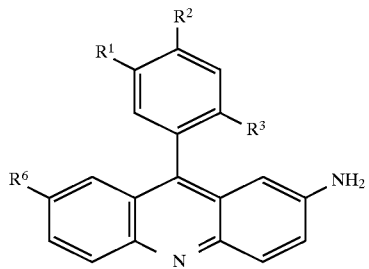

| Compound No. | $R^1$ | $R^2$ | $R^3$ | $R^6$ | M.p., °C. | Yield, % | Appearance |
|---|---|---|---|---|---|---|---|
| 4d | H | H | H | H | 204–206 | 92 | yellow powder |
| 5d, 10d–13d | H | $CH_3$ | H | H | 175–178 | 91 | orange powder |
| 6d | H | $CH_3$ | $CH_3$ | H | 156–159 | 89.5 | orange powder |
| 7d | H | Cl | H | H | 218–220 | 98 | yellow powder |
| 8d | H | $OCH_3$ | H | H | 228–231 | 82 | yellow powder |
| 9d | H | t-$C_4H_9$ | H | H | 302–304 | 62 | yellow powder |
| 18d | $CH_3$ | H | $CH_3$ | $CH_3$ | 102–106 | 92 | orange powder |
| 19d | $CH_3$ | H | $CH_3$ | $OCH_3$ | 110–115 | 86 | orange powder |
| 20d | $CH_3$ | H | $CH_3$ | Cl | 199–200 | 92 | brownish yellow powder |

TABLE V

| Example No. | Compound No. | $R^1$ | $R^2$ | $R^3$ | $R^5$ | $R^6$ | Z | M.p., °C. | Yield, % | Appearance |
|---|---|---|---|---|---|---|---|---|---|---|
| 5 | 4 | H | H | H | $CH_3$ | H | CO | 260–262 | 81 | yellow crystals |
| 6 | 5 | H | $CH_3$ | H | $CH_3$ | H | CO | 218–220 | 89 | yellow crystals |
| 7 | 6 | H | $CH_3$ | $CH_3$ | $CH_3$ | H | CO | 210–212 | 98 | yellow crystals |
| 8 | 7 | H | Cl | H | $CH_3$ | H | CO | 255–257 | 87 | yellow crystals |
| 9 | 8 | H | $OCH_3$ | H | $CH_3$ | H | CO | 230–232 | 60 | yellow crystals |
| 10 | 9 | H | t-$C_4H_9$ | H | $CH_3$ | H | CO | 285–287 | 93 | yellowish green needles |
| 11 | 10 | H | $CH_3$ | H | $HOOC(CH_2)_2$ | H | CO | 258–261 | 71 | yellow powder |
| 12 | 11 | H | $CH_3$ | H | $CH_3$ | H | $SO_2$ | 124–127 | 81 | yellow needles |
| 13 | 13 | H | $CH_3$ | H | $CH_3$-C=$CH_2$ | H | CO | 124–128 | 74 | yellow crystals |
| 14 | 14 | $CH_3$ | H | $CH_3$ | $CH_3$-C=$CH_2$ | H | CO | 208–211 | 50 | light beige crystals |
| 15 | 15 | $CH_3$ | H | $CH_3$ | $CH_3OCH_2$ | H | CO | 181–183 | 54 | yellow powder |
| 16 | 16 | $CH_3$ | H | $CH_3$ | $C_6H_5CH_2$ | H | CO | 208–210 | 84 | light yellow powder |

TABLE V-continued

| Example No. | Compound No. | $R^1$ | $R^2$ | $R^3$ | $R^5$ | $R^6$ | Z | M.p., °C. | Yield, % | Appearance |
|---|---|---|---|---|---|---|---|---|---|---|
| 17 | 17 | $CH_3$ | H | $CH_3$ | $C_6H_5CH=CH$ | H | CO | 118–121 | 92 | light yellow crystals |
| 18 | 18 | $CH_3$ | H | $CH_3$ | $CH_3$ | $CH_3$ | CO | 206–208 | 97 | light yellow powder |
| 19 | 19 | $CH_3$ | H | $CH_3$ | $CH_3$ | $OCH_3$ | CO | 273–275 | 94 | yellow powder |
| 20 | 20 | $CH_3$ | H | $CH_3$ | $CH_3$ | Cl | CO | 233–235 | 96 | yellow powder |

Application Examples 1–9

A basic solution of
- 140.8 pbw of a polymer of methacrylic acid, methyl methacrylate, hexyl methacrylate, butyl acrylate and styrene (22:29:29:15:5), added as 45% strength solution (312.9 pbw) in 1:1 ethanol/butanone,
- 43.2 pbw of trimethylolpropane trisacryloyloxyethyl ether,
- 43.2 pbw of the diurethane obtained from 2 mol of hydroxyethyl acrylate and 1 mol of 2,2,4-trimethylhexamethylene diisocyanate, added as 90% strength solution (48 pbw) in butanone,
- 3.4 pbw of leuco crystal violet,
- 0.1 pbw of Victoria pure blue FGA (C.I. Basic Blue 81) and
- 0.34 pbw of tribromomethyl phenyl sulfone in
- 300 pbw of butanone was prepared. The compounds listed in Table VI were added in the amounts specified therein, which were in each case equivalent to the same molar amounts, as photoinitiators to 75 pbw of this basic solution in each case. Application Example 1 (compound PA) is a comparison example.

The solutions were spun onto biaxially stretched and heat-set 25 μm thick polyethylene terephthalate sheets in such a way that, after drying at 100° C., a layer weight of 45 g/m² was obtained in all cases. The surface of the layer (A) was then laminated with a polyethylene sheet. To determine the photosensitivity, the photoresist layers (A) were laminated, after peeling off the polyethylene sheets, in a commercial laminating device at 115° C. onto 2 mm thick phenolic-resin laminated plates laminated with 35 μm thick copper sheet. The plates were exposed for 6 seconds in a vacuum copying frame using a 5 kW metal-halide lamp. A 13-step exposure wedge having density steps of 0.15 was used as master. After development with a 1% strength soda solution, the copper was completely laid bare under step 9 in all cases.

To test the tendency to diffusion, an appropriately prepared photosensitive material composed of polyester sheet and photoresist layer was cold-laminated onto the polyethylene sheet of a sandwich prepared as above and composed of polyester sheet, photoresist layer A and polyethylene sheet, the photoresist layer (B) having been prepared this time from the basic solution without adding photoinitiator.

The layer structure obtained was compressed between two plates and aged for 48 hours at 40° C. Then the two photoresist layers were separated from the central polyethylene sheet and tested for their UV absorption and photosensitivity. Whether photoinitiator had diffused out of the photoresist layer A through the polyethylene sheet into the initiator-free photoresist during layer B during ageing was determined in this process. It was found that the initiator had diffused into the initiator-free test layer B only from the comparison layer of Example 1.

The determination of the UV absorption of both layers at 360 nm also revealed the same behavior.

To determine the sublimation ability of the photoinitiators, a layer structure was prepared as above with an initiator-containing layer (A) and an initiator-free photoresist layer (B), but instead of the central polyethylene sheet, a 3 mm thick polytetrafluoroethylene plate was used which had a plurality of rectangular openings 25×40 mm in size and which was secured against slipping by strips of double-sided adhesive tape at the edges of the specimen. The entire layer structure was aged for 1 hour in a drying oven at 150° C. The photopolymerizable layers were then tested for their photosensitivity and UV absorption in the region of the openings in the polytetrafluoroethylene plate. The results are shown in Table VI.

TABLE VI

| | | | DIFFUSION EXPERIMENT | | | SUBLIMATION EXPERIMENT | | |
|---|---|---|---|---|---|---|---|---|
| Application Example | Compound | Quantity | UV absorption (360 nm) | Wedge steps | | UV absorption (360 nm) | Wedge steps | |
| No. | No. | pbw | Layer B | Layer A | Layer B | Layer B | Layer A | Layer B |
| 1(V) | PA | 0.050 | yes | 8 | 7–8 | yes | 7 | 5 |
| 2 | 6 | 0.067 | no | 9 | 0 | no | 8 | 0 |
| 3 | 11 | 0.072 | no | 9 | 0 | no | 8 | 0 |
| 4 | 4 | 0.061 | no | 9 | 0 | no | 8 | 0 |
| 5 | 7 | 0.068 | no | 9 | 0 | no | 8 | 0 |
| 6 | 8 | 0.067 | no | 9 | 0 | no | 8 | 0 |
| 7 | 9 | 0.072 | no | 9 | 0 | no | 8 | 0 |
| 8 | 1 | 0.067 | no | 9 | 0 | no | 8 | 0 |
| 9 | 5 | 0.064 | no | 9 | 0 | no | 8 | 0 |

V = comparison example
PA = 9-phenylacridine

Application Examples 10–18

The experimental procedure described in Application Examples 1 to 9 was repeated with photopolymerizable materials for whose preparation the following coating solution was used:

13.4 pbw of a polymer of methacrylic acid, acrylic acid, methyl methacrylate, butyl acrylate and styrene (16:5:42:27:10), added as 50% strength solution (26.8 pbw) in 1:1 ethanol/butanone,
2.8 pbw of trimethylolpropane trisacryloyloxyethyl ether,
2.8 pbw of the diurethane obtained from 2 mol of hydroxyethyl methacrylate and 1 mol of 2,2,4-trimethylhexamethylene diisocyanate,
1.4 pbw of the reaction product obtained from 1 mol of hydroxyethyl methacrylate, 5 mol of ethylene oxide and 1 mol of butyl isocyanate,
y pbw of a compound specified in Table VII,
0.008 pbw of Victoria pure blue FGA,
0.3 pbw of leuco crystal violet and
0.02 pbw of tribromomethyl phenyl sulfone in
15 pbw of ethanol and
15 pbw of butanone.

TABLE VII

| Application Example No. | Compound No. | Quantity y (pbw) |
| --- | --- | --- |
| 10(V) | PA | 0.040 |
| 11 | 6 | 0.053 |
| 12 | 11 | 0.057 |
| 13 | 4 | 0.049 |
| 14 | 7 | 0.054 |
| 15 | 8 | 0.054 |
| 16 | 9 | 0.058 |
| 17 | 1 | 0.053 |
| 18 | 5 | 0.051 |

After exposure for 14 seconds, the copper was completely laid bare in step 9 in all cases. Migration and sublimation of the photoinitiator into the layer B was observed only in Comparison Example 10.

While several embodiments of the invention have been described, it will be understood that it is capable of further modifications, and this application is intended to cover any variations, uses, or adaptations of the invention, following in general the principles of the invention and including such departures from the present disclosure as to come within knowledge or customary practice in the art to which the invention pertains, and as may be applied to the essential features hereinbefore set forth and falling within the scope of the invention or the limits of the appended claims.

The priority document German patent application 195 48 623.4 filed Dec. 23, 1995, is incorporated herein by reference in its entirety.

What is claimed is:

1. A compound of formula I

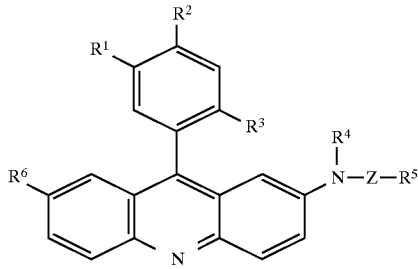

wherein $R^1$, $R^2$, $R^3$ and $R^6$ are identical to or different from one another and are selected from the group consisting of hydrogen, halogen atoms, $C_1$–$C_6$ alkyl, $C_1$–$C_6$ alkoxy, and $C_1$–$C_6$ alkoxyalkyl groups, and wherein at least one of $R^1$, $R^2$, $R^3$ and $R^6$ is a halogen atom, $C_1$–$C_6$ alkyl, $C_1$–$C_6$ alkoxy, or a $C_1$–$C_6$ alkoxyalkyl group;

$R^4$ is a hydrogen atom, an alkyl group containing 1 to 4 carbon atoms or an $SO_2R^5$ radical;

$R^5$ is an alkyl, alkoxy, alkoxyalkyl, carboxyalkyl or alkenyl group each containing up to 6 carbon atoms, an aralkyl group containing 7 to 10 carbon atoms or an aralkenyl group containing 8 to 10 carbon atoms; and Z is a carbonyl or sulfonyl group.

2. A compound as claimed in claim 1, wherein $R^2$ is a hydrogen atom and $R^1$ and $R^3$ are methyl groups.

3. A compound as claimed in claim 1, wherein $R^4$ is a hydrogen atom and Z is a carbonyl group.

4. A compound as claimed in claim 1, wherein $R^5$ is a methyl group.

5. A photopolymerizable mixture, comprising a compound of formula I

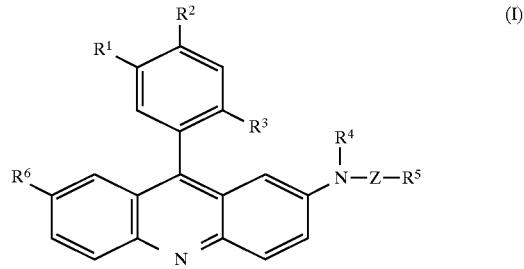

wherein $R^1$, $R^2$, $R^3$ and $R^6$ are identical to or different from one another and are selected from the group consisting of hydrogen, halogen atoms, $C_1$–$C_6$ alkyl, $C_1$–$C_6$ alkoxy, and $C_1$–$C_6$ alkoxyalkyl groups;

$R^4$ is a hydrogen atom, an alkyl group containing 1 to 4 carbon atoms or an $SO_2R^5$ radical;

$R^5$ is an alkyl, alkoxy, alkoxyalkyl, carboxyalkyl or alkenyl group each containing up to 6 carbon atoms, an aralkyl group containing 7 to 10 carbon atoms or an aralkenyl group containing 8 to 10 carbon atoms; and Z is a carbonyl or sulfonyl group as a photoinitiator.

6. A photopolymerizable mixture as claimed in claim 5, further comprising a polymeric binder and an ethylenically unsaturated, free-radical-polymerizable compound.

7. A photopolymerizable mixture as claimed in claim 6, wherein the free-radical-polymerizable compound is an acrylic ester or methacrylic ester of a polyhydric aliphatic alcohol.

8. A photopolymerizable mixture as claimed in claim 6, wherein the polymeric binder is insoluble in water, and soluble or swellable in aqueous alkaline solutions.

9. A process for preparing a compound of formula I

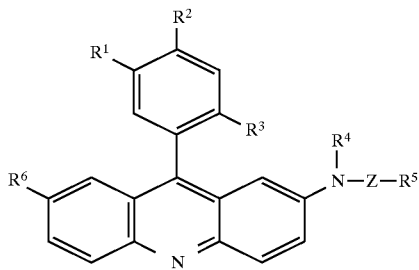
(I)

wherein

- $R^1$, $R^2$, $R^3$ and $R^6$ are identical to or different from one another and are selected from the group consisting of hydrogen, halogen atoms, $C_1$–$C_6$ alkyl, $C_1$–$C_6$ alkoxy, and $C_1$–$C_6$ alkoxyalkyl groups, and wherein at least one of $R^1$, $R^2$, $R^3$ and $R^6$ is a halogen atom, $C_1$–$C_6$ alkyl, $C_1$–$C_6$ alkoxy, or a $C_1$–$C_6$ alkoxyalkyl group;
- $R^4$ is a hydrogen atom, an alkyl group containing 1 to 4 carbon atoms or an $SO_2R^5$ radical;
- $R^5$ is an alkyl, alkoxy, alkoxyalkyl, carboxyalkyl or alkenyl group each containing up to 6 carbon atoms, an aralkyl group containing 7 to 10 carbon atoms or an aralkenyl group containing 8 to 10 carbon atoms; and
- Z is a carbonyl or sulfonyl group;

said process comprising:

converting 2-chloro-5-nitrobenzoic acid into an acid chloride using a chlorinating agent;

reacting the acid chloride with a compound of formula II

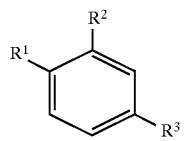
(II)

in the presence of a Friedel-Crafts catalyst to form a substituted benzophenone of formula III;

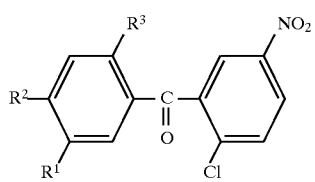
(III)

replacing the 2-chlorine atom of the compound III by an anilino radical by reacting the benzophenone of formula III with an aromatic amine of formula IV,

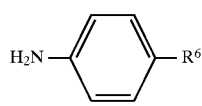
(IV)

to form a secondary amine of formula V;

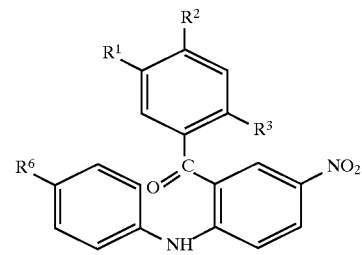
(V)

cyclizing the secondary aromatic amine of formula V, to form 2-nitro-9-arylacridine of formula VI;

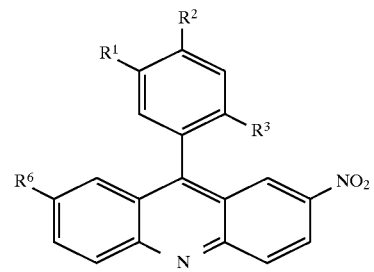
(VI)

reducing the 2-nitro-9-acylacridine compound VI to the corresponding primary amine (VII);

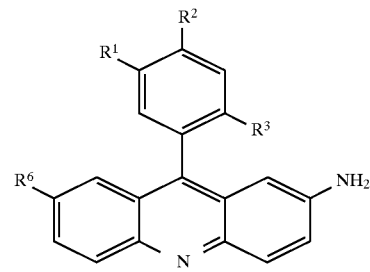
(VII)

reacting the amine VII with an acylating agent $R^5$—Z—X, and optionally with a further acylating agent or an alkylating agent $R^4$—X, where X is a halogen atom.

10. A process as claimed in claim 9, wherein said chlorinating agent is phosphorus pentachloride or thionyl chloride.

11. A process as claimed in claim 9, wherein said Friedel-Crafts catalyst is anhydrous $FeCl_3$.

12. A process as claimed in claim 9, wherein prior to the reaction with the aromatic amine of formula IV, said benzophenone III is diluted with a polar solvent.

13. A process as claimed in claim 9, wherein said secondary aromatic amine of formula V is cyclized in an acidic reaction medium.

14. A process as claimed in claim 9, wherein said 2-nitro-9-phenylacridine of formula VI is reduced to the primary amine VII in either a mixture of ethanol/concentrated hydrochloric acid with $SnCl_2$ or in an acidic aqueous solution with metallic aluminum.

15. A process as claimed in claim 9, wherein said acylating agent is selected from the group consisting of a carboxylic anhydride, a carboxylic acid halide, a carboxylic acid chloride, a carboxylic ester chloride, and an alkyl or arylsulfonyl chloride.

16. A process as claimed in claim 9, wherein the compound III is reacted with an aromatic amine IV, in the presence of sodium acetate.

17. A photopolymerizable mixture as claimed in claim 5, wherein said compound of formula I is present in an amount from 0.01 to 10% by weight, based on the weight of the nonvolatile constitutents of the mixture.

18. A photopolymerizable mixture as claimed in claim 6, wherein the binder is present in an amount from 20 to 90% by weight based on the weight of the mixture.

* * * * *